United States Patent [19]

Sakiyama et al.

[11] Patent Number: 5,273,025
[45] Date of Patent: Dec. 28, 1993

[54] APPARATUS FOR DETECTING INSERTION CONDITION OF ENDOSCOPE

[75] Inventors: Katsunori Sakiyama, Akikawa; Yoshikatsu Nagayama, Sagamihara; Hiroki Hibino; Yutaka Takahashi, both of Hachioji; Sakae Takehana, Machida; Yoshihito Shimizu, Hachioji; Yoshinao Oaki, Hachioji; Koji Koda, Hachioji, all of Japan

[73] Assignee: Olympus Optical Co., Ltd., Tokyo, Japan

[21] Appl. No.: 684,100

[22] Filed: Apr. 12, 1991

[30] Foreign Application Priority Data

Apr. 13, 1990 [JP] Japan ................... 2-98524

[51] Int. Cl.⁵ ............... A61B 1/06; A61B 5/06
[52] U.S. Cl. .................... 128/6; 128/899; 128/737
[58] Field of Search ............ 128/4, 6, 784, 786, 128/653.1, 903, 737, 653.5, 899, 653.2, 653.3, 656, 658, 662.06; 358/98; 600/9–15; 324/219, 246; 175/45

[56] References Cited

U.S. PATENT DOCUMENTS

| 4,173,228 | 11/1979 | Van Steenwyk et al. ...... 128/653.1 |
| 4,176,662 | 12/1979 | Frazer . |
| 4,445,501 | 5/1984 | Bresler ...................... 128/737 X |
| 4,905,698 | 3/1990 | Strohl, Jr. et al. ......... 128/653 R |
| 5,005,592 | 4/1991 | Cartmell .................... 128/899 |
| 5,042,486 | 8/1991 | Pfeiler et al. ............ 128/653.1 |

Primary Examiner—Richard J. Apley
Assistant Examiner—John P. Leubecker
Attorney, Agent, or Firm—Armstrong, Westerman, Hattori, McLeland & Naughton

[57] ABSTRACT

An apparatus is provided for detecting an endoscopic inserting condition. The apparatus includes an irradiation arrangement for applying electromagnetic waves to the inside of an organism from outside the organism, an electromagnetic wave reception arrangement which is disposed in an insert section of an endoscope for producing an electromagnetic signal, and a detection arrangement receiving the electromagnetic signal produced by the electromagnetic wave reception arrangement, for detecting the insertion orientation of the endoscope on the basis of the received electromagnetic signal.

20 Claims, 7 Drawing Sheets

APPARATUS FOR DETECTING INSERTION CONDITION OF ENDOSCOPE

BACKGROUND OF THE INVENTION

1. Field of the Invention

This invention relates to an apparatus for detecting endoscopic insertion condition which makes it possible to detect the condition of the inserted section of an endoscope when it is in the tubular body cavity to be examined.

2. Description of the Related Art

An endoscope is an apparatus equipped with a thin and flexible insert section, which is inserted into the internal section to be examined, which is a tubular body cavity, in order that the internal section to be examined may be observed and any requisite measures be taken. Tubular body cavities, e.g., the large and the small intestines, are full of twists and turns, so that it is by no means easy for the operator to know exactly where the endoscopic insert section has reached in the body cavity or what posture it has taken there.

In view of this, it has conventionally been the practice to X-ray, from the exterior, the internal section to be examined so as to detect the position, posture, etc. of the insert section in the tubular body cavity.

X-raying, however, is not entirely harmless to the human body, and thus such a method can be applied to only a limited number of body portions. Thus, the X-raying is not always an ideal detection means for detecting endoscopic inserting condition.

U.S. Pat. No. 4,176,662 discloses an apparatus for locating the position of the tip section of an an endoscope when it is in the body cavity. In accordance with this prior-art technique, a transmission section for transmitting electromagnetic waves or supersonic waves is provided at the tip section of an endoscope, and a reception antenna is provided on that portion of the endoscope which is on the outside of the body cavity. Thus, with this apparatus, electromagnetic waves or supersonic waves can be emitted from the transmission section at the tip of the endoscope and received by the reception antenna on the outside of the body cavity, thereby enabling the position of the tip section of the endoscope to be located. A problem with this prior-art technique is that a component requiring a relatively large power output (i.e., the transmission section) is inserted into the body cavity, which means, like the X-raying method mentioned above, that it is not always ideal as a means for detecting an endoscopic inserting condition.

SUMMARY OF THE INVENTION

An object of this invention is to provide an apparatus for detecting endoscopic insertion location which enables the condition of the insert section of an endoscope to be detected when it is in the body cavity without physiologically affecting the human body.

Another object of this invention is to provide an apparatus for detecting endoscopic insertion location which enables the actual posture of the insert section of an endoscope when it is in the body cavity to be known without having to locate an endoscopic antenna section inserted into the body cavity.

Still another object of this invention is to provide an apparatus for detecting endoscopic insertion location wherein a plurality of electromagnetic wave reception means are arranged in the axial direction of an endoscopic insert section in such a manner as to avoid mutual interference therebetween so that they can be arranged at small intervals, thereby making it possible to detect endoscopic insertion location with high accuracy.

In summary, the apparatus for detecting endoscopic insertion location of this invention comprises an irradiation means for applying electromagnetic waves to the inside of an organism from the outside, an electromagnetic wave reception means provided in the insert section of an endoscope, and a means for detecting the inserting condition of the endoscope on the basis of a reception signal supplied from the electromagnetic wave reception means.

The above and other objects and advantages of the present invention will become apparent from the detailed description given below.

BRIEF DESCRIPTION OF THE DRAWINGS

FIGS. 1 to 3 show a first embodiment of the apparatus of this invention, of which:

FIGS. 4 to 8 show a second embodiment of the apparatus of this invention, of which:

DETAILED DESCRIPTION OF THE PREFERRED EMBODIMENTS

The first embodiment of this invention will be described with reference to FIGS. 1 to 3.

Figure 1:
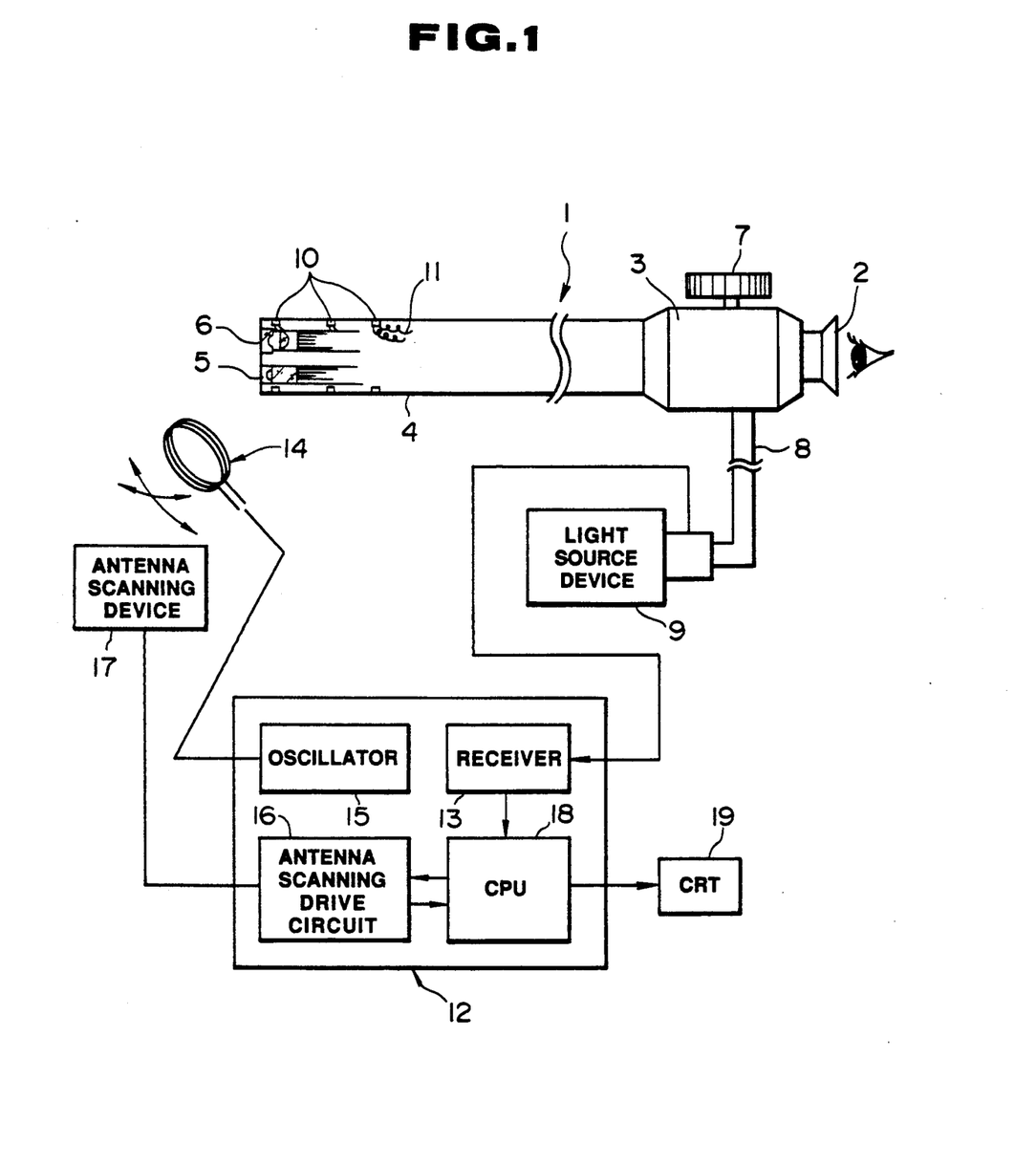
FIG. 1 is a schematic diagram showing the overall construction of the first embodiment.

The endoscope 1 shown in FIG. 1 includes an operating section 3, which also serves as the grip and is equipped with an eyepiece section 2. A thin and long insert section 4 extends forwardly from this operating section 3. This insert section 4 is introduced into the body cavity via the mouth, anus, etc. so that the section to be examined may be observed or the requisite measures be taken. The insert section 4 is composed of: an elongated flexible section capable of being inserted into tubular body cavities having many turns and twists; a bending section connected to the tip of this flexible section; and a tip section connected to the tip of the bending section and equipped with a light emitting window 5 constituting the illumination optical system, and an observation window 6 constituting the observation optical system. By turning an angle knob 7 provided on the operating section 3, the bending section can be bent, enabling the tip section to be directed as the operator wishes.

A universal chord 8 extends from the operating section 3 and is connected to a light source device 9 for supplying the illumination light. The endoscope 1 shown is an optical-type endoscope in which the image for observation formed by the objective optical system behind the observation window 6 is transmitted, by means of an image transmission means, to the eyepiece section 2, with which the image is directly observed. The application of this invention, however, is not limited to this type of endoscope. It is naturally also applicable to an electronic endoscope in which the image for observation formed by the objective optical system undergoes photoelectric transfer by means of a solid-state imaging device to provide an imaging signal, which is transmitted to an external video processor, where it is signal-processed to enable the image to be displayed on the monitor.

Provided within the insert section 4 of the endoscope are a plurality of reception antennae serving as position detecting sensors. These reception antennae consist, e.g., of loop-like coils 10, which are arranged at least at such intervals as to avoid mutual interference therebetween. For a pattern in which the coils 10 are varied in resonant frequencies, all coils have different resonant frequencies. Thus, by appropriately varying the resonance frequency among them, these coils 10 can be arranged at smaller intervals, whereby the operator is enabled to obtain more accurate positional information. When it receives electromagnetic waves, each of the coils 10 generates an induced voltage. Accordingly, a cable 11 for outputting this voltage is connected to each of the coils 10. These cables 11 are connected through the insert section 4, the operating section 3, and the universal chord 8 to a receiver 13 which is provided inside an inserting condition detecting section 12. Provided within this inserting condition detecting section 12 is an oscillator 15 for supplying high frequency waves to an antenna 14, which serves as the transmission antenna for emitting electromagnetic waves toward the coils 10. Further provided in the above section 12 is an antenna scanning drive circuit 16 for varying the orientation of the transmission antenna 14 with respect to the coils 10. This circuit 16 is connected to an antenna scanning device 17. The antenna scanning drive circuit 16 and the receiver 13 are connected to a CPU 18 which is provided in the detecting section 12. This CPU 18 stores information on the intensity of the induced voltage, which varies in accordance with the orientation of the transmission antenna 14 with respect to the coils 10. At the same time, this CPU 18 supplies the antenna scanning drive circuit 16 with information for varying the orientation of the antenna 14 with respect to the coils 10. That is, the CPU 18 controls the antenna scanning drive circuit 16 as previously programmed to obtain those orientations of the transmission antenna 14 at which the induced voltage of a coil 10 is maximum and minimum, respectively, and detects the point of intersection of that electromagnetic wave direction in which the induced voltage of this coil 10 is maximum and that in which it is minimum. This point of intersection, which corresponds to the position of the coil 10 concerned, is signal-processed and supplied to a CRT 19 for display. A detailed description of this detecting operation will be given with reference to the second embodiment which is described below.

Figure 2A:
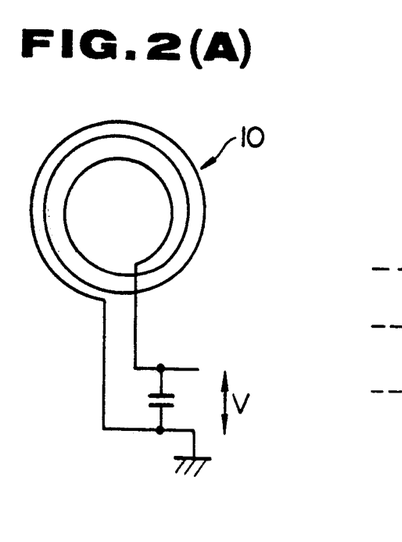
FIGS. 2(A) to 2(D) are diagrams illustrating the operational principles thereof.
Figure 2B:
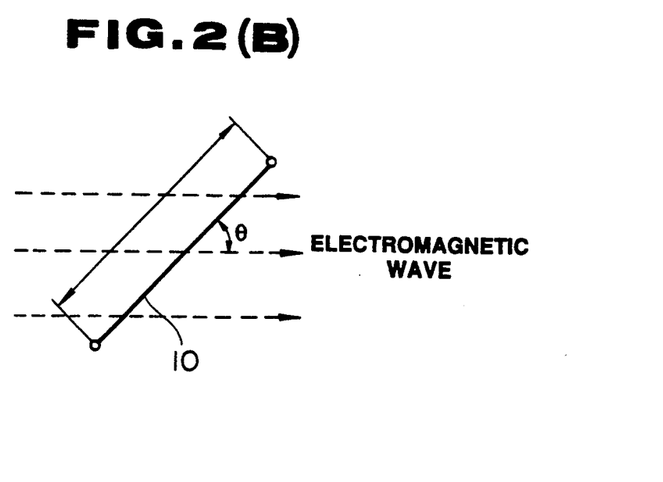

The fact that the position of each coil 10 can be obtained from the point of intersection of that electromagnetic wave direction, i.e., that orientation of the transmission antenna 14, which corresponds to the maximum induced voltage of that coil and that which corresponds to the minimum one, will be understood from the following explanation:

FIG. 2(A) shows a coil 10, and FIG. 2(B) shows the coil as placed in an electromagnetic field.

Assuming that the electromagnetic wave is a vertically polarized wave corresponding to the area A of the coil, the induced voltage V generated therein can be expressed as:

$$V = 2\pi N \cdot E \cdot \frac{A}{\lambda} \cdot \cos\theta \ [V] \quad (1)$$

where E=the field strength of the electromagnetic wave [V/Cm]; N=the total number of turns of the coil; $\theta$=the angle defined by the plane of the coil and the traveling direction of the electromagnetic wave [rad].

Figure 2C:
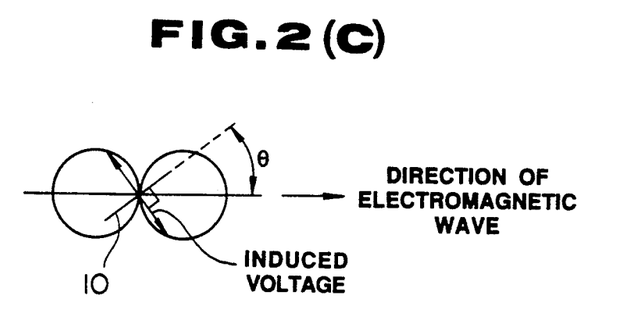

As shown in equation (1), the induced voltage varies depending on $\theta$. Thus, graphically represented, $\theta$ and the induced voltage exhibit a figure-of-eight characteristic, as shown in FIG. 2(C).

Figure 2D:
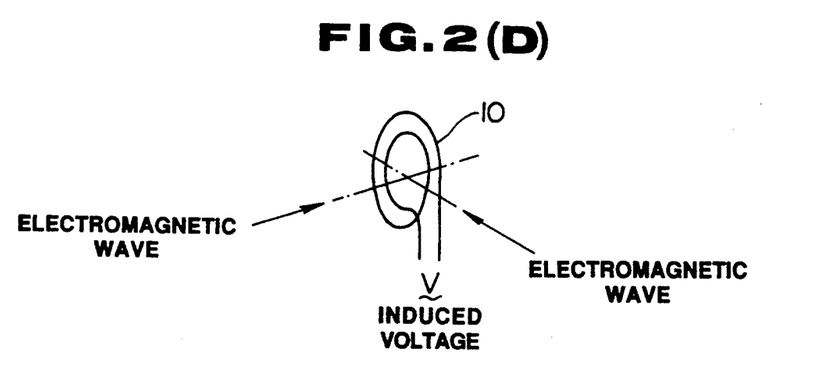

Therefore, provided that the coil 10 remains fixed, the position of this coil can be obtained, as shown in FIG. 2(D), by varying the electromagnetic wave direction so as to locate those antenna orientations at which the induced voltage is maximum and minimum, respectively.

Figure 3:
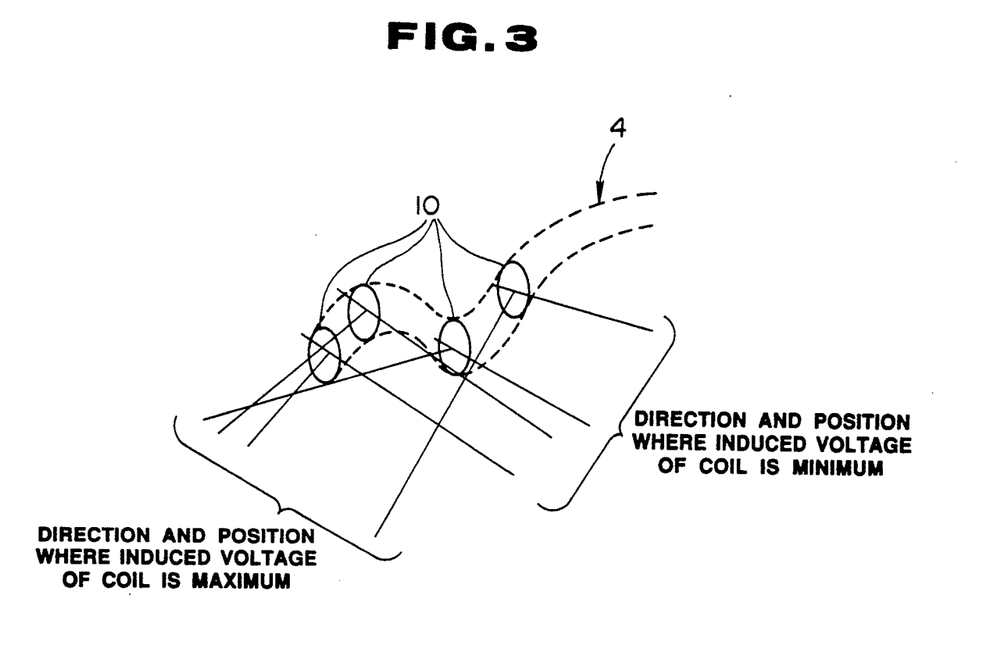
FIG. 3 is a diagram illustrating the coil position locating operation.

Accordingly, when a plurality of coils 10 are arranged in the insert section 4, as shown in FIG. 3, the position of each coil 10 can be detected as the point of intersection of that direction of the electromagnetic wave from the transmission antenna 14 in which the induced voltage of that coil is maximum and that direction of the same in which it is minimum. When connected together, the respective positions of these coils 10 give the posture of the insert section 4, and, through signal-processing, this posture can be displayed through the CRT 19.

The configuration of the coils is not limited to a round one; square coils or directional antennae such as dipole antennae may also be employed as the coils. The transmission antenna may be, for example, of a helical, a parabola, or a phased-array type, which is strongly directional. Further, it is desirable that the apparatus of this invention should be used in a room whose walls, etc. are equipped with electromagnetic-wave-absorbing plates in order that scattering of the electromagnetic waves by the wall surfaces, etc. may be avoided.

Next, the second embodiment will be described with reference to FIGS. 4 to 8.

Figure 4:
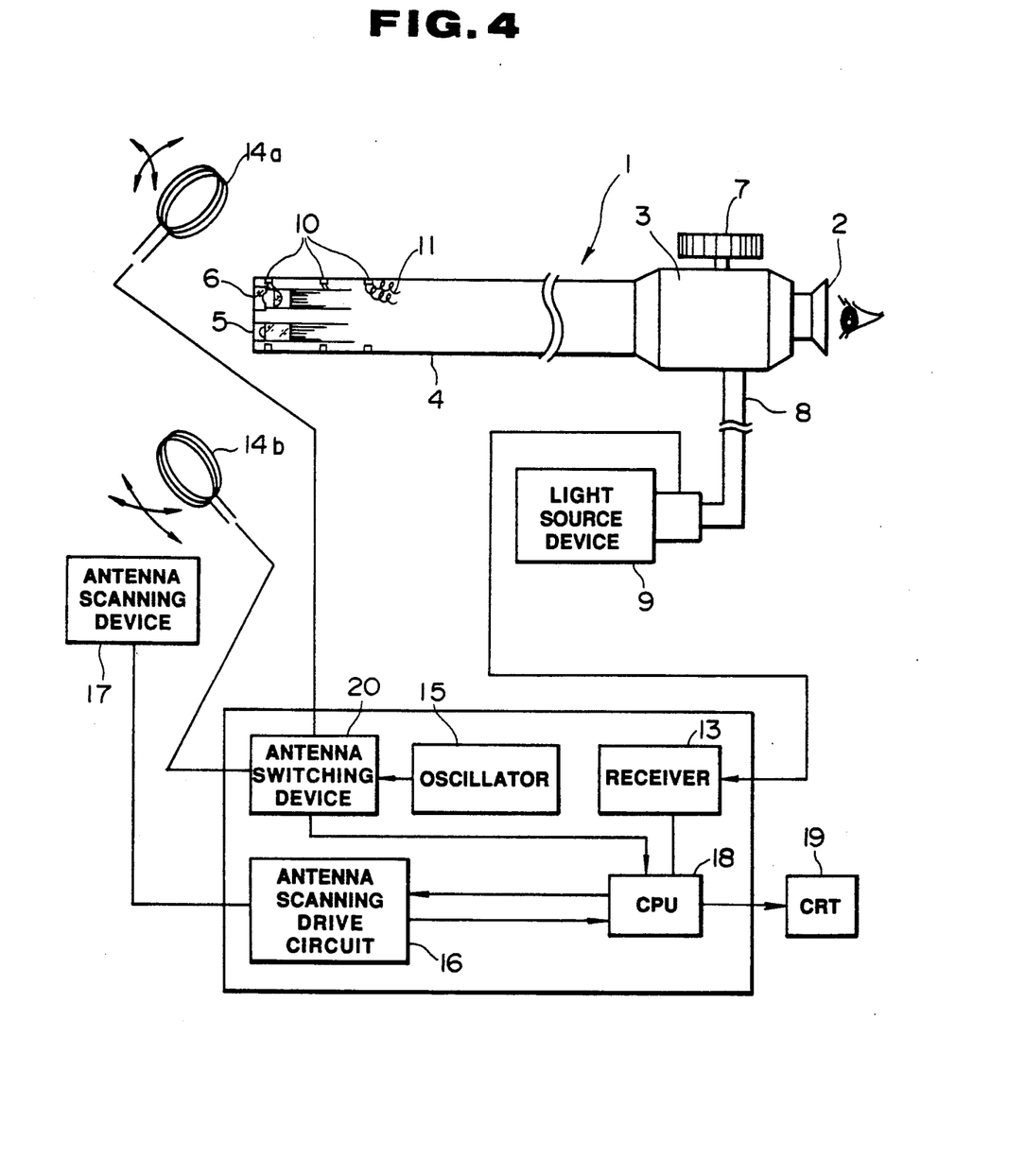
FIG. 4 is a schematic diagram showing the overall construction of the second embodiment.
Figure 5:
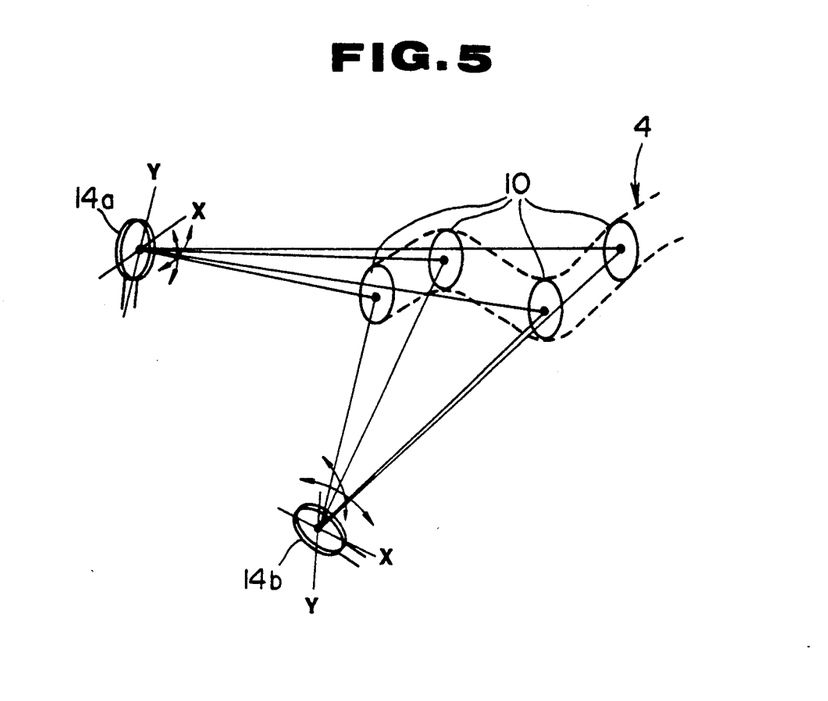
FIG. 5 is a diagram illustrating the operation thereof.

This embodiment uses a plurality of transmission antennae. In the example shown, two transmission antennae, 14a and 14b, are used. By scanning these antennae 14a and 14b, those electromagnetic wave directions in which the induced voltages generated by the electromagnetic waves from these antennae are maximum are obtained for each coil 10, thereby detecting the position of each coil 10, which corresponds to the point of intersection of the above electromagnetic wave directions of the antennae 14a and 14b.

Figure 6:
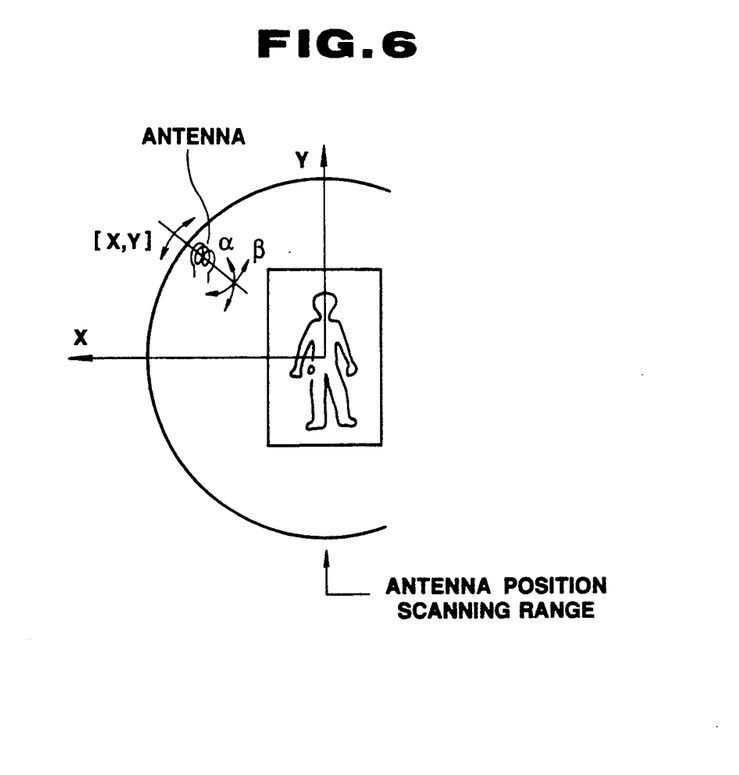
FIG. 6 is a diagram illustrating the scanning range of the transmission antenna.

Using two transmission antennae, 14a and 14b, the apparatus of this embodiment is equipped with an antenna switching device 20, with which the electromagnetic wave emission from one antenna is changed to that from the other. As shown in FIGS. 4 and 6, the transmission antennae 14a and 14b may be scanned around the X- and Y-axes with their positions being fixed. With the transmission antenna 14 shown in FIG. 6, positional scanning can be performed approximately 180° around the patient.

Next, with reference to the flowcharts of FIGS. 7 and 8, the procedures for detecting endoscopic inserting condition in the body cavity will be described.

In Steps S1 and S2, the transmission and reception antennae are selected, and, in Step S3, the oscillator is turned ON. In Step S4, the transmission antenna is scanned by turning it in the vertical direction so as to obtain the α angle of the point where the reception intensity S of the reception antenna is maximum. Next, in Step S5, the transmission antenna is scanned by turning it laterally so as to obtain the β angle of the point at which the reception intensity S of the reception antenna is maximum. Subsequently, in Step S6, the α angle obtained in Step S4, the β angle obtained in Step S5, and the X-Y coordinates of the transmission antenna shown in FIG. 6, are stored in memory. Then, in Step S7, a judgment is made as to whether the procedures of Steps S4 to S6 have been completed or not. If they have, the procedure moves on to Step S8, and, if not, the next reception antenna is selected in Step S9, repeating the procedures of Step S4 onward. Further, in Step 8, the X-Y coordinates of the transmission antenna are moved a predetermined distance within the antenna position scanning range to make a judgment as to whether the procedures of Steps S4 to S6 have been completed or not. If they have, the procedure moves on to subroutine (A), and, if not, the transmission antenna is moved to the next predetermined position in Step S10, repeating the procedures of Steps S4 to S8.

In subroutine (A), the position of the reception antenna is obtained on the basis of the respective reception antenna intensities at the different transmission antenna positions obtained through the main routine. In Step S11, the data on the first reception antenna is selected. Then, obtained in Step S12 are the above-mentioned α and β angles at the X-Y coordinates corresponding to the maximum reception intensity S of the reception antenna. Then, in Step S14, the three-dimensional position of the reception antenna is obtained from the point of intersection of the transmission antenna beam directions obtained in the above steps, S12 and S13. Next, in Step S15, a judgment is made as to whether the three-dimensional position has been obtained for all the reception antennae or not. If there remain some reception antennae for which the three-dimensional position has not been obtained yet, the next reception antenna is selected in Step S16, repeating the procedures of Steps S12 to S15. If it is judged that the three-dimensional position has been obtained for all the reception antennae, a three-dimensional display of the endoscopic inserting condition is given through the CRT in Step S17, and, with this, the detecting operation is ended.

Figure 7:
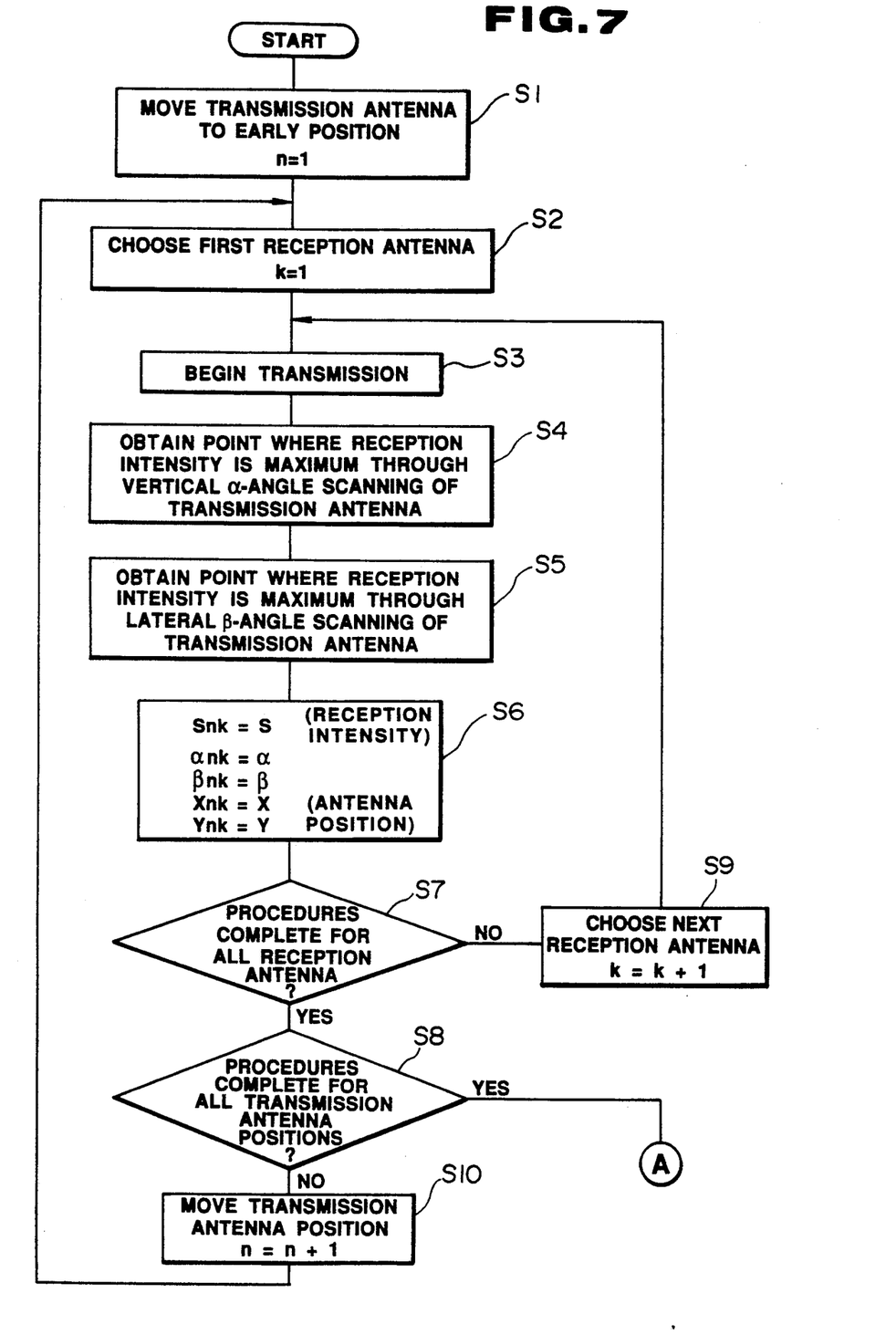
FIGS. 7 and 8 are flowcharts illustrating an operational example wherein the endoscopic inserting condition is detected and displayed through a CRT.
Figure 8:
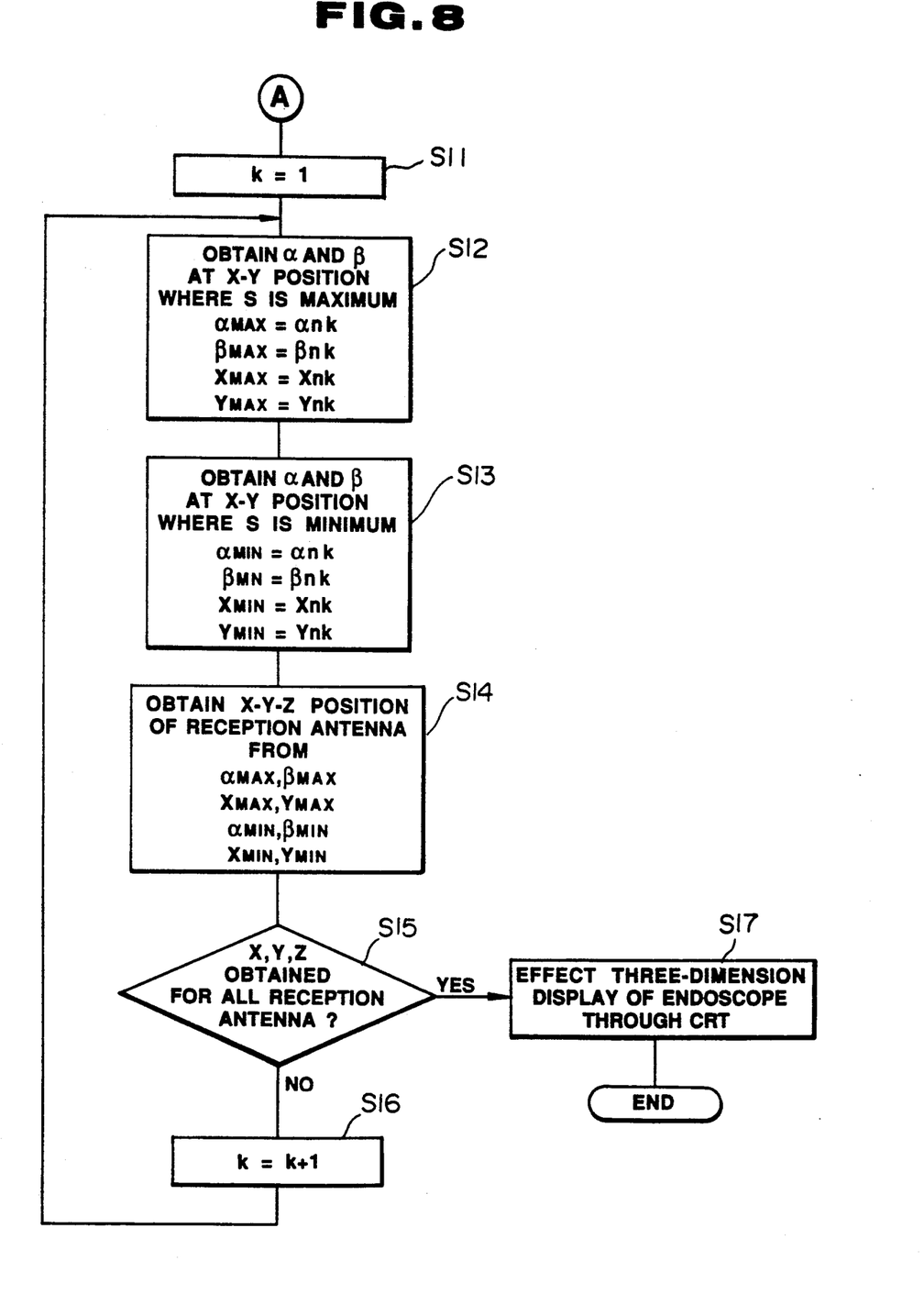

The flowcharts shown in FIGS. 7 and 8 apply to the first embodiment, wherein a single transmission antenna is used. In the case of the second embodiment, wherein a plurality of transmission antennae are used, the transmission antennae is to be selected from two of them, and, in subroutine (A) for obtaining the reception antenna position, the position of the reception antenna is obtained from the point of intersection of the transmission antenna beam directions in which the intensity of the reception from the two transmission antennae is maximum.

It is obvious that this invention allows a variety of embodiments to be constructed based thereon without departing from the spirit and scope thereof. The scope of this invention is limited solely by the appended claims.

What is claimed is:

1. An apparatus for detecting an endoscopic inserting condition, comprising:

a flexible insertion tube;
an irradiation means for applying electromagnetic waves to the inside of an organism from outside the organism;
an electromagnetic wave reception means which is disposed in said flexible insertion tube of an insert section of an endoscope, for producing electromagnetic signals in response to said irradiation means; said electromagnetic wave reception means including a plurality of reception sections which are disposed intermittently along an axial direction of said flexible insertion tube, said reception sections each comprising a different, independent coil and producing its own distinct electromagnetic signal; and
a detection means operably connected to said irradiation means and said reception means and receiving the electromagnetic signals produced by said electromagnetic wave reception means, for detecting the posture of each of said reception sections on the basis of the received said electromagnetic signals.

2. An apparatus for detecting endoscopic inserting condition as claimed in claim 1, wherein said reception sections consist of coils positioned inside said insert section and wound along the periphery thereof.

3. An apparatus for detecting an endoscopic inserting condition as claimed in claim 2, wherein every one of said coils has a unique resonant frequency.

4. An apparatus for detecting endoscopic inserting condition as claimed in claim 2, wherein said detection means further includes a detector for detecting an induced voltage that is generated in accordance with the intensity of the electromagnetic waves received by said coils.

5. An apparatus for detecting endoscopic inserting condition as claimed in claim 4, wherein said coils are connected to said detector through an electric cable extending through the insert section of the endoscope and a universal chord.

6. An apparatus for detecting endoscopic inserting condition as claimed in claim 1, wherein said irradiation means is equipped with at least two electromagnetic wave oscillating sections arranged at different positions.

7. An apparatus for detecting endoscopic inserting condition as claimed in claim 1, wherein said irradiation means is equipped with a single electromagnetic wave oscillating section.

8. An apparatus for detecting endoscopic inserting condition as claimed in claim 1, wherein said irradiation means has a magnetic wave oscillating section which is adapted to move in such a manner as to generate electromagnetic waves from at least two different positions.

9. An apparatus for detecting endoscopic inserting condition as claimed in claim 1, wherein said irradiation means includes an electromagnetic wave generating section which is adapted to generate directional electromagnetic waves, with their directivity being variable.

10. An apparatus for detecting endoscopic inserting condition as claimed in claim 7, wherein said irradiation means includes a scanning means which supports said electromagnetic wave generating section and which varies the directivity thereof.

11. An apparatus for detecting endoscopic inserting condition as claimed in claim 1, wherein said irradiation means includes an oscillator for generating a high frequency current, and an antenna which is connected to said oscillator and to which said high frequency current is supplied to generate electromagnetic waves.

12. An apparatus for detecting an endoscopic inserting condition provided at least in the vicinity of a tip of an insert section of an endoscope, comprising:
   a flexible insertion tube having a distal end;
   an electromagnetic wave reception means for generating induced voltages upon receiving an electromagnetic wave, said electromagnetic wave reception means disposed in said flexible insertion tube of an insert section of an endoscope and including a plurality of reception sections disposed intermittently along an axial direction proximal to the distal end of said flexible insertion tube, said plurality of reception sections each comprising a different, independent coil and producing its own distinct electromagnetic signal;
   an electromagnetic wave generating means for applying electromagnetic waves to the inside of an organism from the outside of the organism and which is capable of emitting first and second electromagnetic waves from at least two positions;
   a scanning means operably connected to said electromagnetic wave generating means, for varying the respective directivities of said first and second electromagnetic waves generated by said electromagnetic wave generating means; and
   a position detecting means operably connected to said reception means and said scanning means, for obtaining the posture of each of said reception sections on the basis of the directivities of said first and second electromagnetic waves emitted from said electromagnetic wave generating means and the induced voltages from said electromagnetic wave reception means corresponding thereto.

13. An apparatus for detecting endoscopic inserting condition as claimed in claim 12, wherein said electromagnetic wave generating means is equipped at least with a first electromagnetic wave generating section for generating a first electromagnetic wave, and a second electromagnetic wave generating section for generating a second electromagnetic wave which is provided at a position different from that of said first electromagnetic wave generating section.

14. An apparatus for detecting endoscopic inserting condition as claimed in claim 15, wherein said first and second electromagnetic wave generating sections generate electromagnetic waves of the same frequency.

15. An apparatus for detecting endoscopic inserting condition as claimed in claim 14, wherein each of said coils have a unique resonant frequency and, said electromagnetic wave generating sections is capable of outputting at least frequencies corresponding to the resonance frequencies of said coils.

16. An apparatus for detecting endoscopic inserting condition as claimed in claim 12, wherein said electromagnetic wave generating means includes a single electromagnetic wave generating section, and a means for varying the position of said electromagnetic wave generating section so as to cause said electromagnetic wave generating section to generate said first and second electromagnetic waves.

17. An apparatus for detecting endoscopic inserting condition as claimed in claim 12, wherein said position detecting means is adapted to obtain the respective directivities of said first and second electromagnetic waves when the induced voltage from said electromagnetic wave detection means is maximum, obtaining the point of intersection of these directivities.

18. An apparatus for detecting endoscopic inserting condition as claimed in claim 16, wherein said position detecting means is adapted to obtain the position of said electromagnetic wave detection means from the respective directivities of said first and second electromagnetic waves which are generated by said electromagnetic wave generating means when the induced voltage from said electromagnetic wave detection means is maximum and minimum.

19. An endoscope of the type allowing detection of an insertion location, comprising:
   an insert section including a flexible insertion tube;
   an illuminating light transmitting means disposed inside said insert section, for transmitting illuminating light from a base side of said insert section to a tip of said insert section;
   an image transmitting means provided inside said insert section, for transmitting an image obtained at said tip of said insert section to said base side of said insert section; and
   a plurality of electromagnetic wave detecting coils which are electrically independent of each other and are spaced apart along an axial direction of said insert section, said plurality of electromagnetic wave detecting coils being disposed inside said flexible insertion tube of said insert section of the endoscope and which are disposed intermittently along an axial direction of said flexible insertion tube and are partially wound along a periphery of said insert section in such a manner so as to surround said illuminating light transmitting means and said image transmitting means, said plurality of electromagnetic wave detecting coils each comprising a different, independent coil and producing its own distinct electromagnetic signal upon reception of electromagnetic waves.

20. An endoscope as claimed in claim 19, wherein every one of said coils has a unique resonant frequency.

* * * * *